US009052301B2

(12) United States Patent
Azuma et al.

(10) Patent No.: US 9,052,301 B2
(45) Date of Patent: Jun. 9, 2015

(54) AUTOMATIC ANALYZER

(75) Inventors: Shinji Azuma, Hitachinaka (JP); Teruhiro Yamano, Hitachinaka (JP); Hiroshi Watanabe, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 139 days.

(21) Appl. No.: 13/809,161

(22) PCT Filed: Jun. 30, 2011

(86) PCT No.: PCT/JP2011/065060
§ 371 (c)(1),
(2), (4) Date: Jan. 8, 2013

(87) PCT Pub. No.: WO2012/005168
PCT Pub. Date: Jan. 12, 2012

(65) Prior Publication Data
US 2013/0115134 A1    May 9, 2013

(30) Foreign Application Priority Data

Jul. 9, 2010   (JP) .................................. 2010-156311

(51) Int. Cl.
*G01N 35/04*   (2006.01)
*G01N 35/10*   (2006.01)

(52) U.S. Cl.
CPC ........ *G01N 35/1065* (2013.01); *G01N 35/1011* (2013.01); *G01N 35/04* (2013.01); *G01N 2035/0491* (2013.01)

(58) Field of Classification Search
CPC .......... G01N 35/1011; G01N 35/1065; G01N 35/04; G01N 35/2035
See application file for complete search history.

(56) References Cited

U.S. PATENT DOCUMENTS

| 5,051,238 A | * | 9/1991 | Umetsu et al. .................. 422/64 |
| 5,827,479 A | | 10/1998 | Yamazaki et al. |
| 2005/0207938 A1 | | 9/2005 | Hanawa et al. |

FOREIGN PATENT DOCUMENTS

| DE | 197 01 505 A1 | 7/1997 |
| JP | 09-196925 A | 7/1997 |
| JP | 2005-37171 A | 2/2005 |
| JP | 2006-300847 A | 11/2006 |
| JP | 2008-020361 A | 1/2008 |
| JP | 2010-145284 A | 7/2010 |
| JP | 2010-151519 A | 7/2010 |
| WO | WO 2008/007598 A1 | 1/2008 |

OTHER PUBLICATIONS

English translation of International Preliminary Report on Patentability for International Patent Application No. PCT/JP2011/065060, Feb. 21, 2013.

* cited by examiner

*Primary Examiner* — Jill Warden
(74) *Attorney, Agent, or Firm* — Miles & Stockbridge P.C.

(57) ABSTRACT

An automatic analyzer is provided which applies a position detection mechanism to at least either a reagent probe or a reagent container transfer mechanism, thereby performing control on or inhibiting a reset operation (initialization) of either the reagent probe or the reagent container transfer mechanism to prevent the transfer thereof. This allows a reagent transport mechanism attached to the automatic analyzer automatically replacing reagent containers to be configured to move at the same height as those of various units including the reagent probe. The automatic analyzer is thus made small in size and allowed to operate without problems.

6 Claims, 5 Drawing Sheets

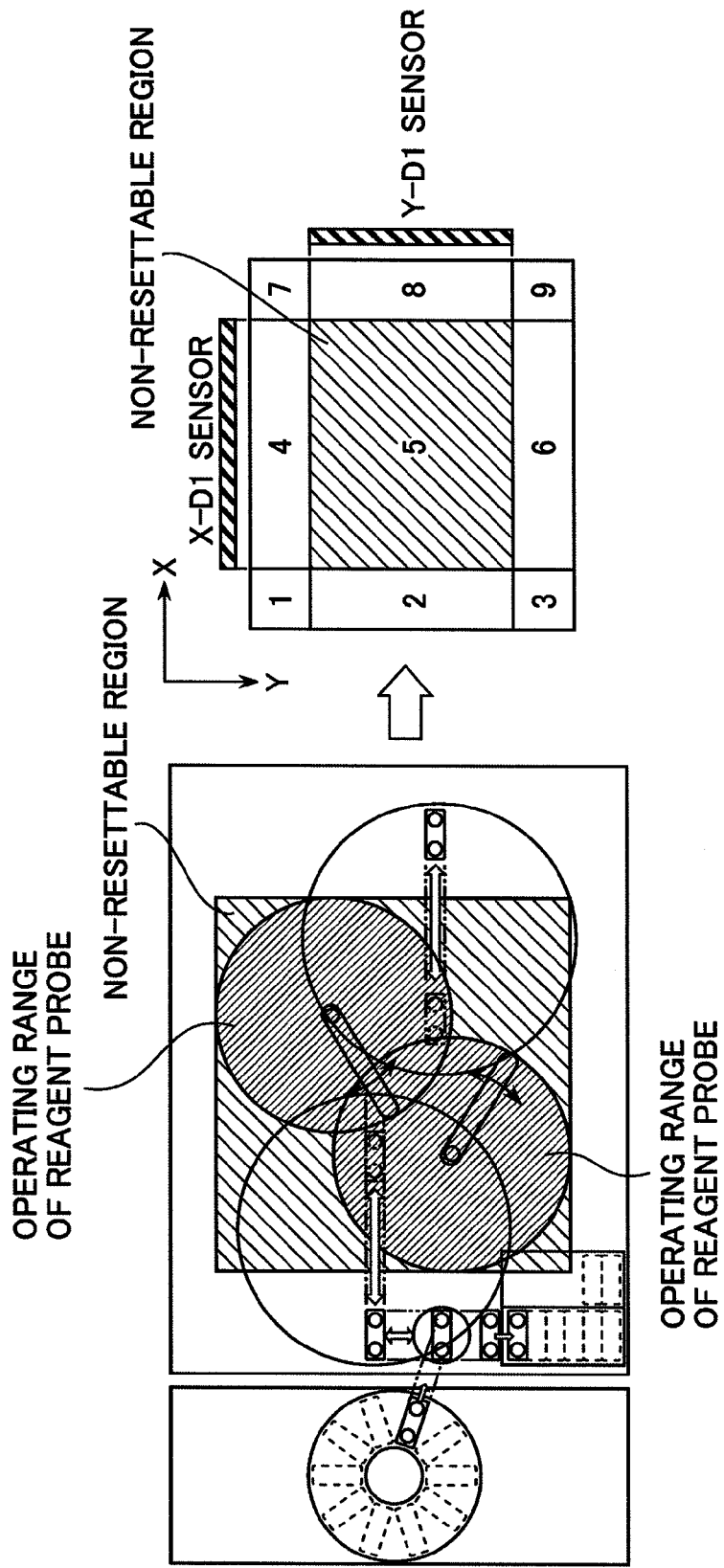

AUTOMATIC ANALYZER

TECHNICAL FIELD

This invention relates to an automatic analyzer for analyzing specimens of blood, urine or the like. More particularly, the invention relates to an automatic analyzer furnished with a mechanism for replacing reagent containers.

BACKGROUND ART

Automatic analyzers recently need to have their reagent containers replaced more frequently than before due to higher rates at which reagents have been consumed because of the growing number of specimens to be processed and the increasing number of items to be measured. Meanwhile, there has been a need for reducing as much as possible the workload on operators so as to lower costs notably labor cost. Thus it has been desired to simplify the work of replacing reagent containers.

Also raised have been the speeds at which automatic analyzer process specimens. It has been desired that interruptions of analyzing operations be minimized so that the equipment may continuously operate even during the work of reagent replacement.

Patent Document 1 discloses an automatic analyzer which includes replacement reagent storage means 2 apart from reagent storage means 1 in an analysis unit and which has reagent transport means interposed between the reagent storage means 1 and the replacement reagent storage means 2, thereby simplifying the work of reagent replacement and minimizing interruptions of analytical work.

PRIOR ART LITERATURE

Patent Document

Patent Document 1: JP-2005-037171-A

SUMMARY OF THE INVENTION

Problems to be Solved by the Invention

In the automatic analyzer disclosed in Patent Document 1, if the reagent transport mechanism is configured to move at the same height as the reagent probe, the mechanism and the probe can interfere with one another. If the reagent transport mechanism and the reagent probe are configured not to interfere with one another, the equipment size can become inordinately large.

An object of this invention is to provide an automatic analyzer having a reagent transport mechanism for automatically replacing reagent containers, the reagent transport mechanism being moved at the same height as those of diverse units including the reagent probe so that the equipment size may be kept small and that the analyzer may operate without problems.

Means for Solving the Problems

In achieving the above object, the present invention may be configured as follows:

An automatic analyzer is provided including: a reagent container which contains a reagent; reagent container placement mechanisms which place a plurality of the reagent containers; a reagent dispensing probe with a mechanism for transferring the position of a nozzle which aspirates a predetermined amount of a reagent held in the reagent containers on the reagent container placement mechanisms, before discharging the aspirated reagent into a reaction container, and a reagent container transfer mechanism which transfers the reagent containers to the reagent container placement mechanisms. The reagent dispensing probe and the reagent container transfer mechanism are configured to move within the same range of heights, and to interfere with one another at least at a predetermined position. The automatic analyzer further includes: a position detection mechanism which detects the position of at least either the reagent dispensing probe or the reagent container transfer mechanism, and a control mechanism which, if the position detection mechanism detects that at least either the reagent dispensing probe or the reagent container transfer mechanism is in a predetermined position, performs control not to transfer at least either the reagent dispensing probe or the reagent container transfer mechanism.

At the start of analysis or maintenance, the automatic analyzer performs reset operations of various units for operation check thereof.

At that point, if the reagent transport mechanism of the analyzer is inside an operating range of the reagent probe, then an alarm is activated and control is performed to inhibit the reset operations.

The reagent transport mechanism should preferably be furnished with a detector, a detection plate, etc., as means for determining whether the reagent transport mechanism is in a non-resettable region.

Effects of the Invention

In the automatic analyzer that has the reagent transport mechanism moving at the same height as that of the reagent probe, the detector and detection plate attached to the reagent transport mechanism permit the analyzer to detect the position of the reagent transport mechanism. This allows the reagent transport mechanism to transport reagent cassettes without interfering with the reagent probe.

BRIEF DESCRIPTION OF THE DRAWINGS

FIG. 1 is a plan view of an automatic analyzer according to the present invention.
[FIG. 2A]
FIG. 2A is a plan view showing non-resettable regions of the automatic analyzer of this invention.
FIG. 2B is a flowchart of processes up to the activation of an alarm in effect when a reset is designated on the automatic analyzer of this invention.
FIG. 3A is a plan view showing non-resettable regions of the automatic analyzer of this invention.
FIG. 3B is a flowchart of processes up to the activation of an alarm in effect when a reset is designated on the automatic analyzer of this invention.

MODE FOR CARRYING OUT THE INVENTION

Some preferred embodiments of this invention are explained below in detail by reference to the accompanying drawings.

Figure 1:
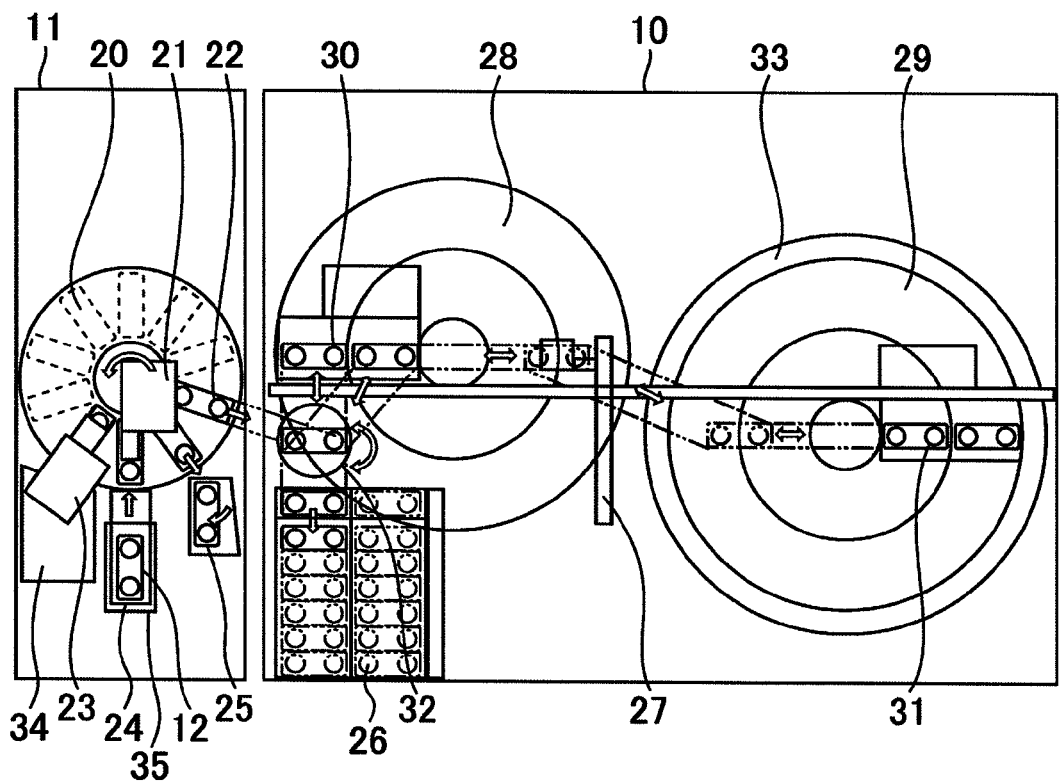
[FIG. 1]

FIG. 1 is a plan view of the automatic analyzer.

An automatic analyzer is made up of an analysis unit 10 and a buffer unit 11.

The analysis unit 10 includes reagent cabinets A 28 and B 29, a reagent transport mechanism 27 that takes a reagent container 12 from the buffer unit 11 and transports the container to the reagent cabinet A 28 or B 29, and a reagent ejection and stowing mechanism 26 that ejects the reagent container 12 from the analysis unit 10. The buffer unit 11 includes a replenishing reagent cabinet 20 that temporarily stores replenishing reagents and a reagent ejection mechanism 25 that ejects the reagent containers.

Explained below is the procedure for transporting the reagent containers 12 using the equipment above.

First, when an operator places a reagent container 12 at a reagent injection port, not shown, a reagent injection mechanism 24 transfers the reagent container 12 to the replenishing reagent cabinet 20.

The reagent container 12 transferred to the replenishing reagent cabinet 20 carries an RFID tag on which is recorded such information as the remaining reagent amount, a lot number, and a use-by date. The information is read by a reagent information read mechanism 21 mounted on the replenishing reagent cabinet 20, and is stored into a control computer, not shown. At this point, the reagent container 12 is ejected by the reagent ejection mechanism 25 in the buffer unit 11 if the container in question is determined to be unusable for analysis by the control computer for such reasons as expiration of the use-by date or an insufficient remaining amount of the reagent.

The reagent for which a reagent replenishment request has been issued is transferred to a cap opening position of a reagent cap opening mechanism 23 mounted beforehand on the replenishing reagent cabinet 20. In the cap opening position, the reagent cap of the reagent container 12 is opened, and the cap is discarded into a reagent cap disposal box 34.

The reagent cassette 12 with its reagent cap opened is sent to a reagent container transfer position inside the replenishing reagent cabinet 20. Once placed in that position, the reagent cassette 12 is sent from the buffer unit 11 to the analysis unit 10 by a reagent container transfer mechanism 22. The replacing of reagents is timed to be performed typically in an idle cycle between exhausted reagents or an interval between the dispensing of a first reagent and that of a second reagent, provided the replacing will not cause a shortage of reagents. If the replenishment of a reagent cannot be completed in time, the sampling of specimens is suspended, the reagent is dispensed to the specimens yet to be sampled, and then the reagent is replenished. In any case, the equipment is currently in analyzing mode and not temporarily stopped to have the reagent replenished. Thus the idle time resulting from the suspension of analysis may be shortened.

The reagent cassette 12 transferred to the analysis unit 10 is placed on a reagent rotation mechanism 32 installed in the analysis unit 10. The reagent rotation mechanism 32 reorients the reagent bottle 12 in a direction necessary for mounting onto the reagent cabinet A 28 or B 29.

The reoriented reagent bottle 12 is transferred by the reagent transport mechanism 27 to the reagent cabinet A 28 or B 29 from which a reagent replacement request has been made. After transferring the reagent bottle 12 to the reagent cabinet A 28 or B 29, the reagent transport mechanism 27 transfers any reagent container 12 of which the remaining reagent is insufficient and which needs to be replaced from the reagent cabinet A28 or B29 back to the reagent ejection and stowing mechanism 26. The reagent ejection and stowing mechanism 26 transfers the reagent container 12 to a reagent stowing part inside the reagent ejection and stowing mechanism 26; the reagent container 12 is stowed there until the operator removes it.

The automatic analyzer furnished with the reagent transport mechanism 27 above tends to be bulky in external dimensions because of this mechanism. However, there has been a growing need in recent years for smaller-sized analyzers. Even when equipped with the reagent transport mechanism 27, the analyzer needs to remain small in external size. In view of that need, the analysis unit 10 may be provided in which the reagent probe is moved within the same range of heights as the reagent transport mechanism 27 so that the external dimensions of the analyzer remain the same.

Where the reagent transport mechanism 27 is moved at the same height as the reagent probe, there is a risk of interference therebetween. In order to avoid the interference, non-resettable regions are established.

FIG. 2A is a plan view showing non-resettable regions of the automatic analyzer equipped with the reagent transport mechanism according to this invention. One sensor is provided for each of the directions involved so that the analysis unit may be divided into nine blocks. This arrangement makes it possible to identify whether the reagent transport mechanism is in a non-resettable region. If the reagent transport mechanism is found in a non-resettable region, an alarm is activated.

Figure 2B:
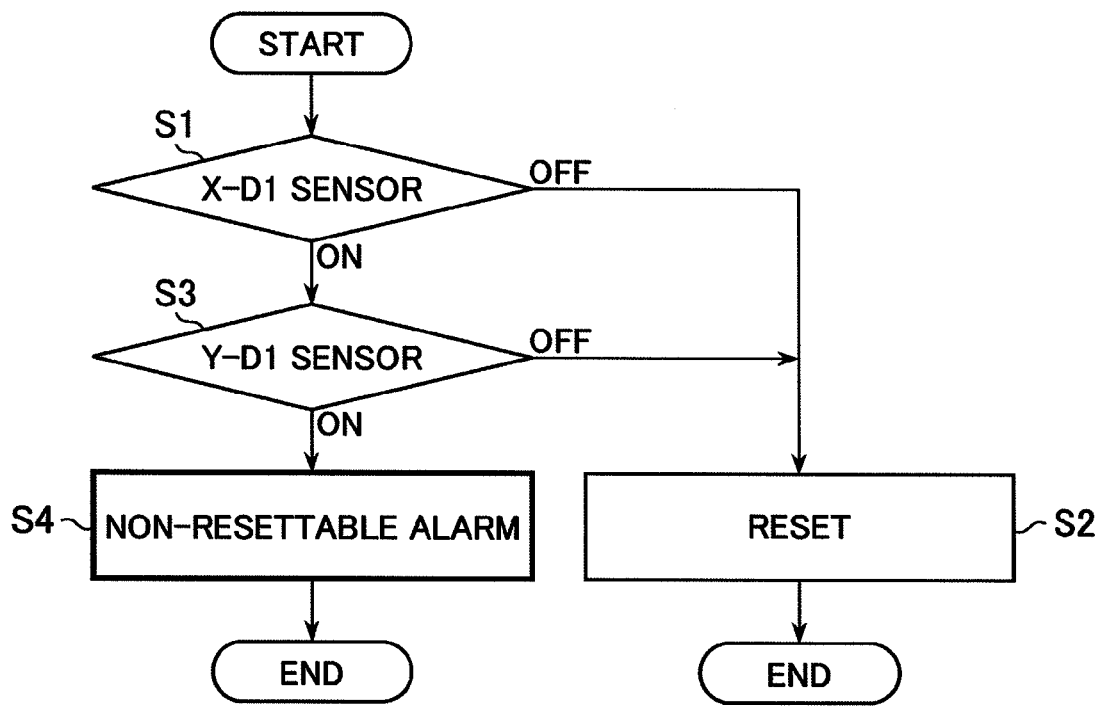
[FIG. 2B]

FIG. 2B is a flowchart of processes up to the activation of an alarm in effect when a reset is designated. First, the status of an X-D1 sensor attached to the X-axis of the reagent transport mechanism is checked (S1). If this status is OFF (block 1, 2, 3, 7, 8 or 9), there is no risk of interference between the reagent transport mechanism and the reagent probe. In this case, a reset is performed (S2). If the status above is ON, the status of a Y-D1 sensor attached to the Y-axis is checked (S3). If this status is OFF (block 4 or 6), a reset is performed (S2). If this status is ON (block 5), that means the reagent transport mechanism is within the operating range of the reagent probe and there is a risk of interference between the two components. In that case, a "non-resettable region" alarm is activated (S4). The alarm may involve giving an indication such as "MOVE MANUALLY TO RESETTABLE REGION" prompting manual movement of the transport mechanism to a resettable region. After the movement, a reset may be performed.

The sensors used here may be of any type including transmission-type sensors or reflection-type sensors, as long as they are capable of determining status.

Figure 3A:
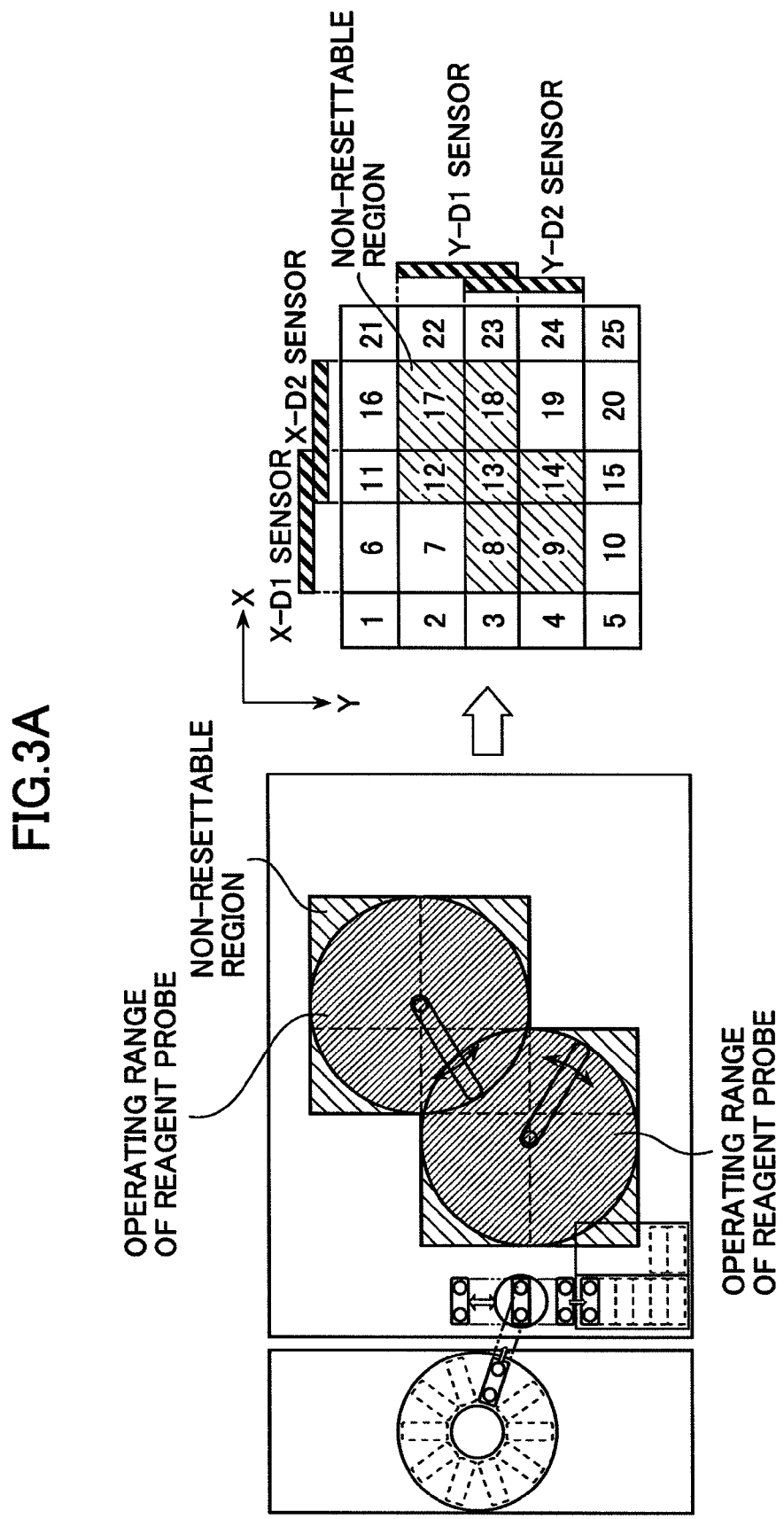
[FIG. 3A]

FIG. 3A is a plan view showing non-resettable regions of the automatic analyzer of this invention. Two sensors are provided for each of the directions involved so that the analysis unit may be divided into 25 blocks. This arrangement makes the non-resettable regions narrower each than those in FIG. 2A (blocks 7 and 19). The larger the number of sensors installed, the narrower the resulting blocks constituting the non-resettable regions that are narrower.

Figure 3B:
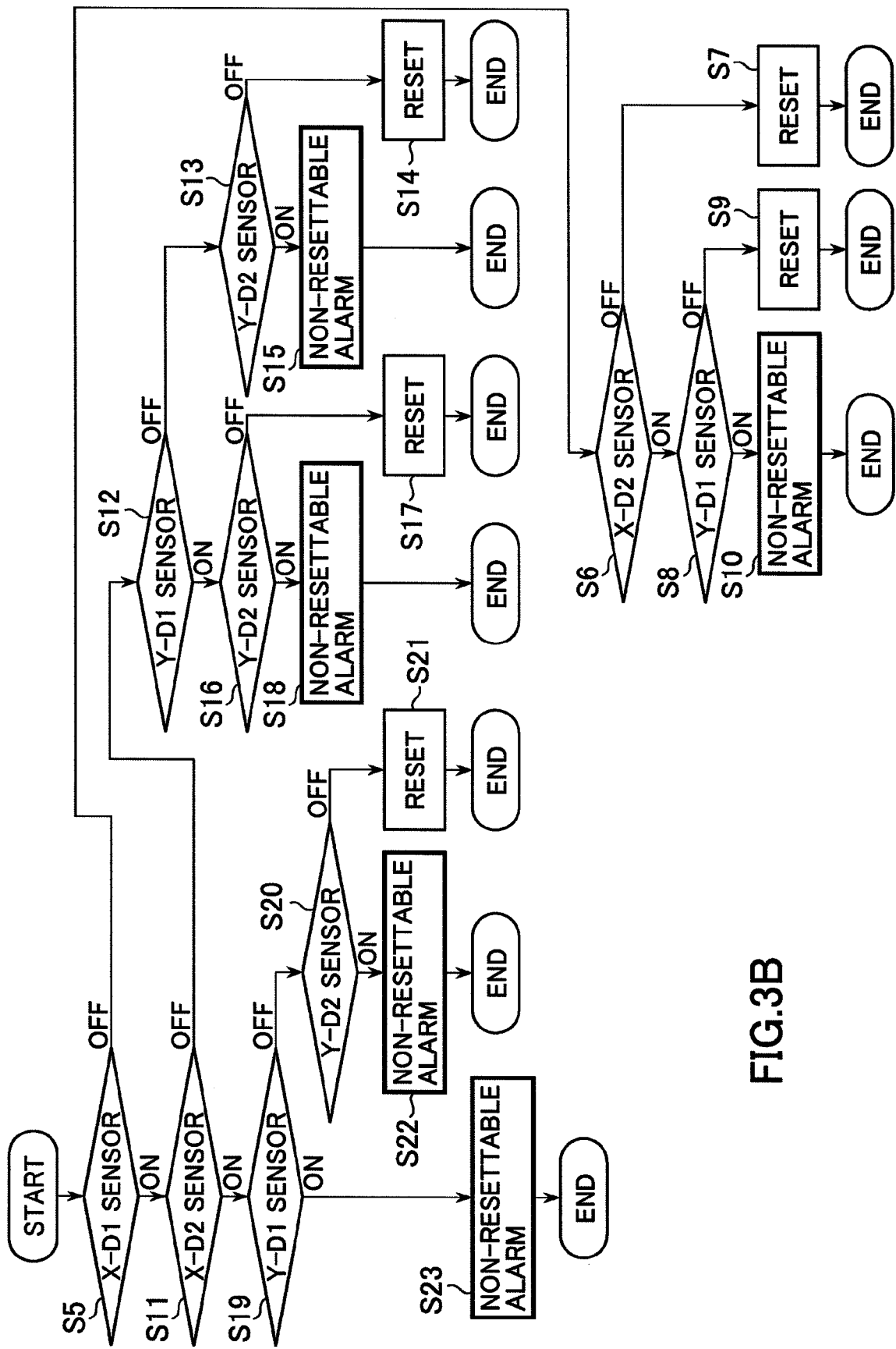
[FIG. 3B]

FIG. 3B is a flowchart of processes up to the activation of an alarm in effect when a reset is designated. First, the status of an X-D1 sensor attached to the X-axis of the reagent transport mechanism is checked (S5). If this status is OFF, the status of an X-D2 sensor attached to the same X-axis is checked (S6). If this status is OFF (block 1, 2, 3, 4, 5, 21, 22, 23, 24 or 25), there is no risk of interference between the reagent transport mechanism and the reagent probe. In this case, a reset is performed (S7).

If the status is ON in S6, the status of a Y-D1 sensor attached to the Y-axis is checked (S8). If this status is OFF (block 16, 19 or 20), a reset is performed (S9). If this status is ON (block 17 or 18), the "non-resettable region" alarm is activated (S10).

If the status is ON in S5, the status of the X-D2 sensor is checked (S11). If this status is OFF, the status of the Y-D1 sensor is checked (S12). If this status is OFF, the status of the Y-D2 sensor is checked (S13). If this status is OFF (block 6 or 10), a reset is performed (S14). If this status is ON (block 9), the "non-resettable region" alarm is activated (S15).

If the status is ON in S11, the status of the Y-D2 sensor is checked (S16). If this status is OFF (block 7), a reset is performed (S17). If this status is ON (block 8), the "non-resettable region" alarm is activated (S18).

If the status is ON in S10, the status of the Y-D1 sensor is checked (S19). If this status is OFF, the status of the Y-D2 sensor is checked (S20). If this status is OFF (block 11 or 15), a reset is performed (S21). If this status is ON (block 14), the "non-resettable region" alarm is activated (S22).

If the status is ON in S18 (block 12 or 13), the "non-resettable region" alarm is activated (S23).

The above procedure can perform reset processing in 25 blocks. If three sensors were set up for each direction, there would be 49 blocks; if four sensors were installed for each direction, there would be 81 blocks; and more sensors would make the non-resettable regions progressively narrower still. However, in view of the growing complexity of logic, space constraints, and cost restrictions, the number of sensors should preferably be two per direction.

One way of narrowing the non-resettable regions is by reviewing the operating ranges of the reagent probe. Whereas FIGS. 2A, 2B, 3A and 3B show all operating ranges of the reagent probe to be non-resettable regions, the position of the reagent probe can be restricted since sensors are usually attached also to the reagent probe. It is then possible to further narrow the non-resettable regions by clarifying the positional relationship between the reagent probe and the reagent transport mechanism.

DESCRIPTION OF REFERENCE NUMERALS

10 Analysis unit
11 Buffer unit
12 Reagent container (also called reagent cassette or reagent bottle)
20 Replenishing reagent cabinet
21 Reagent information read mechanism
22 Reagent transfer mechanism
23 Reagent cap opening mechanism
24 Reagent injection mechanism
25 Reagent ejection mechanism
26 Reagent ejection and stowing mechanism
27 Reagent transport mechanism
28 Reagent cabinet A
29 Reagent cabinet B
30 Reagent injection port A
31 Reagent injection port B
32 Reagent rotation mechanism
33 Reaction mechanism
34 Reagent cap disposal box
35 Reagent injection port

The invention claimed is:

1. An automatic analyzer comprising:
a reagent container which contains a reagent;
reagent container placement mechanisms which place a plurality of the reagent containers;
a reagent dispensing probe with a mechanism for transferring the position of a nozzle, which aspirates a predetermined amount of a reagent held in the reagent containers on the reagent container placement mechanisms, before discharging the aspirated reagent into a reaction container; and
a reagent container transfer mechanism which transfers the reagent containers to the reagent container placement mechanisms, wherein the reagent dispensing probe and the reagent container transfer mechanism are configured to move within the same range of heights and to interfere with one another at least at a predetermined position;
a position detection mechanism which detects the position of the reagent dispensing probe and the reagent container transfer mechanism; and
a control mechanism which, if the position detection mechanism detects that the reagent dispensing probe is in the predetermined position, performs control not to move the reagent container transfer mechanism, and, if the position detection mechanism detects that the reagent container transfer mechanism is in the predetermined position, performs control not to move the reagent dispensing probe.

2. The automatic analyzer according to claim 1, wherein the position detection mechanism includes a detection plate installed along a transfer locus of either the reagent dispensing probe or the reagent container transfer mechanism, and a detector which detects the detection plate attached to either the reagent dispensing probe or the reagent container transfer mechanism.

3. The automatic analyzer according to claim 1, wherein the reagent dispensing probe includes an arm part which rotates around a rotation axis, and a nozzle attached to the arm part.

4. The automatic analyzer according to claim 1, wherein the reagent container transfer mechanism includes a holding part for taking hold of the reagent containers and a holding part transfer mechanism for transferring the holding part.

5. The automatic analyzer according to claim 1, wherein the position detection mechanism divides a detection area into a plurality of regions so as to detect the region in which either the reagent dispensing probe or the reagent container transfer mechanism is present.

6. The automatic analyzer according to claim 1, wherein, if the position detection mechanism detects that the reagent dispensing probe is in the predetermined position, then the position detection mechanism prevents transfer of reagent container transfer mechanism by inhibiting a reset operation thereof, and, if the position detection mechanism detects that the reagent container transfer mechanism is in the predetermined position, then the position detection mechanism prevents transfer of the reagent dispensing probe by inhibiting the reset operation thereof, the reset operation including moving to the predetermined position.

* * * * *